United States Patent [19]
Heikkilä

[11] Patent Number: 5,840,039
[45] Date of Patent: Nov. 24, 1998

[54] METHOD AND APPARATUS IN CONNECTION WITH MEASURING THE HEARTBEAT RATE OF A PERSON

[75] Inventor: Ilkka Heikkilä, Oulu, Finland

[73] Assignee: Polar Electro Oy, Kempele, Finland

[21] Appl. No.: 860,502

[22] PCT Filed: Dec. 28, 1995

[86] PCT No.: PCT/FI95/00714

§ 371 Date: Jun. 27, 1997

§ 102(e) Date: Jun. 27, 1997

[87] PCT Pub. No.: WO96/20641

PCT Pub. Date: Jul. 11, 1996

[30] Foreign Application Priority Data

Dec. 29, 1994 [FI] Finland ..................................... 946164
May 31, 1995 [FI] Finland ..................................... 952656

[51] Int. Cl.⁶ .................................................. A61B 5/0456
[52] U.S. Cl. ............................................ 600/519; 600/521
[58] Field of Search ................................. 128/702–708; 482/8, 9, 900–902; 600/515–521

[56] References Cited

U.S. PATENT DOCUMENTS

| | | |
|---|---|---|
| 4,367,752 | 1/1983 | Jimenez et al. |
| 4,566,461 | 1/1986 | Lubell et al. |
| 5,117,833 | 6/1992 | Albert et al. |
| 5,265,617 | 11/1993 | Verrier et al. |
| 5,277,189 | 1/1994 | Jacobs |
| 5,291,400 | 3/1994 | Gilham ..................................... 128/702 |
| 5,323,784 | 6/1994 | Shu |
| 5,339,822 | 8/1994 | Taylor et al. |
| 5,423,325 | 6/1995 | Burton ..................................... 128/702 |

FOREIGN PATENT DOCUMENTS

| | | |
|---|---|---|
| 3209850 C2 | 9/1983 | Germany. |
| 3439238 A1 | 5/1985 | Germany. |
| WO 90/09144 | 8/1990 | WIPO. |

*Primary Examiner*—Jeffrey R. Jastrzab
*Attorney, Agent, or Firm*—Hoffmann & Baron, LLP

[57] ABSTRACT

The present invention relates to a method and apparatus in connection with measuring the heartbeat rate of a person. In the method, the ECG signal of the person and the timing moment of at least one ECG signal waveform, such as the QRS complex, are measured with a heartbeat rate monitor. The average heartbeat rate frequency of the heartbeat rate is calculated from the ECG signal. Heartbeat rate variation information proportional to the magnitude of the heartbeat rate variation or to that of the total or partial power of a spectrum derived from the heartbeat rate is provided by means of a mathematical function. The heartbeat rate variation information is displayed on the display of the heartbeat rate monitor together with the average heartbeat rate frequency.

24 Claims, 5 Drawing Sheets

$RR_1 = t_2 - t_1, RR_2 = t_3 - t_2, \ldots$

METHOD AND APPARATUS IN CONNECTION WITH MEASURING THE HEARTBEAT RATE OF A PERSON

BACKGROUND OF THE INVENTION

1. Field of the Invention

The present invention relates to a method and apparatus in connection with measuring the heartbeat rate of a person.

2. Brief Description of the Prior Art

Heartbeat rate measurement is based on monitoring cardiac function. When contracting, a heart produces a series of electric pulses, which can be measured in a body. The measurement and analysis of such a signal is referred to as electrocardiography (ECG). The actual signal is referred to as an ECG signal. In an ECG signal, it is possible to distinguish phases resulting from different operational stages of the heart. These portions are the so-called P, Q, R, S, T and U-waves.

In known solutions, a heartbeat rate monitor shows on its display mainly average heartbeat rate information only, which is calculated as an average from a suitable number of single pulsations. However, there is need to render the heartbeat rate monitors more versatile. In existing heartbeat rate monitors which filter heartbeat rate, the averaging which levels instantaneous heartbeat rate variation prevents the heartbeat rate measurement information from being analyzed in more detail. In signal processing, averaging means low pass filtering, which as used in this connection cuts the fast variation signal away from the heartbeat rate signal. The known solutions do not provide sufficiently multi-faceted information.

Due to the variation in the sympathetic-parasympathetic balance of the autonomic nervous system, variations around the average heartbeat rate level occur constantly in heartbeat rate. The variation in heartbeat rate is caused by the function of the cardiovascular control system. The main reasons for the variation are respiratory arrhythmia, variation caused by blood pressure control, and variation caused by the heat balance control of the system. Among these, the most significant and causing the greatest variation is respiratory arrhythmia. The transmitting nervous systems of heartbeat rate variation can be distinguished by means of heartbeat rate variation frequency analysis. At the present time, the sympathetic nervous system is considered to be slow; it is hardly capable of transmitting frequencies higher than 0.15 Hz. Instead, the operation of the parasympathetic nervous system is fast, wherefore frequencies higher than the above-mentioned threshold frequency are transmitted through the parasympathetic nervous system.

SUMMARY OF THE INVENTION

The object of the present invention is to provide a new type of method and apparatus, with the use of which the problems associated with the known solutions are avoided.

The invention is characterized by what is defined in the claims below.

Many advantages are achieved with the invention. Measuring heartbeat rate variation and showing the measurement result on the display of the heartbeat rate monitor provide important additional information on the operation of a human body and nervous system, especially on the degree of relaxation of a human. By using heartbeat rate variation according to the invention for defining the degree of relaxation, it is possible to implement individual monitoring which is sufficiently multi-faceted and accurate for the needs of a person. The invention thus enables real-time and wireless monitoring of heartbeat rate variation, whereby the invention provides us with more information without difficult measurements carried out in laboratories. A great heartbeat rate variation is an indication that the parasympathetic nervous system functions, which generally corresponds to a relaxed state of a system. As for a small value, it indicates that the sympathetic nervous system is active, which is related to physical or mental stress. Thus, by measuring heartbeat rate variation, it is possible to monitor the state of the autonomic nervous system.

BRIEF DESCRIPTION OF THE DRAWINGS

In the following, the invention will be described in more detail by means of examples with reference to the accompanying drawings, in which.

DESCRIPTION OF PREFERRED EMBODIMENTS

Figure 1:
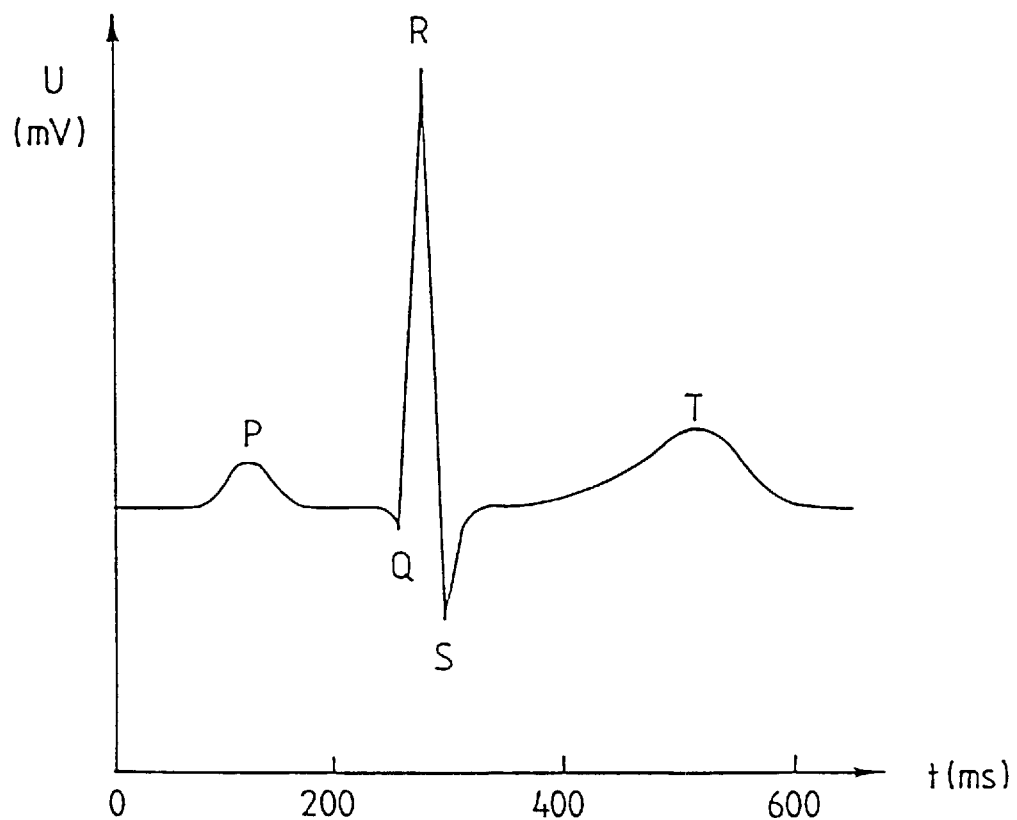
FIG. 1 shows the shape of an ECG signal caused by heartbeat rate.

FIG. 1 shows a typical ECG signal caused by heartbeat rate as presented in a time-voltage coordinate system. The above-mentioned P, Q, R, S, and T-waves can be distinguished in each signal by an accurate measurement. The highest value R represents the maximum point of an ECG signal, and the pulsation defined by the points Q, R and S, i.e. the QRS complex, represents the most easily distinguishable part of the ECG signal. The interval between two successive R peak values is often referred to as the R—R interval of the ECG signal. A P-wave is caused by the contraction of the atria. When the atria contract, the ventricles are filled with blood. The QRS complex formed by the peaks of three waves, defining the shape of the R peak of the ECG signal, is produced when the ventricles contract. The right ventricle thus pumps blood from veins to the lungs, and the left ventricle pumps blood from the lungs to arteries. The repolarization of the ventricle muscles causes a T-wave, which is lower and more even than the R peak. The periods between the waves depend on the speed of propagation of the nervous stimulus in the heart.

In a healthy human, the ECG signal is between 1 and 2 mV in amplitude as measured on the skin. For instance, the amplitude value and duration given for an R peak in literature are 1.6 mV and 90 ms, whereas the corresponding values for a P-wave are 0.25 mV and 110 ms. When the heartbeat rate accelerates as a result of exertion, the durations and amplitudes of the different components of the ECG signal remain almost unchanged. It is thus known that the accurate measurement of heartbeat rate and related phenomena is possible by analyzing the ECG signal of heartbeat rate.

The easiest starting point for determining the timing point of an ECG signal accurately is the detection of the QRS complex. In a disturbance-free situation, the QRS complex can be detected in a fairly simple manner by means of a peak value detector. To reduce the number of disturbances occurring in practical situations, some type of filtering is used in accurate analyses. The filtering may take place by using a band-pass filter, adapted filter, or pattern recognition.

Figure 2:
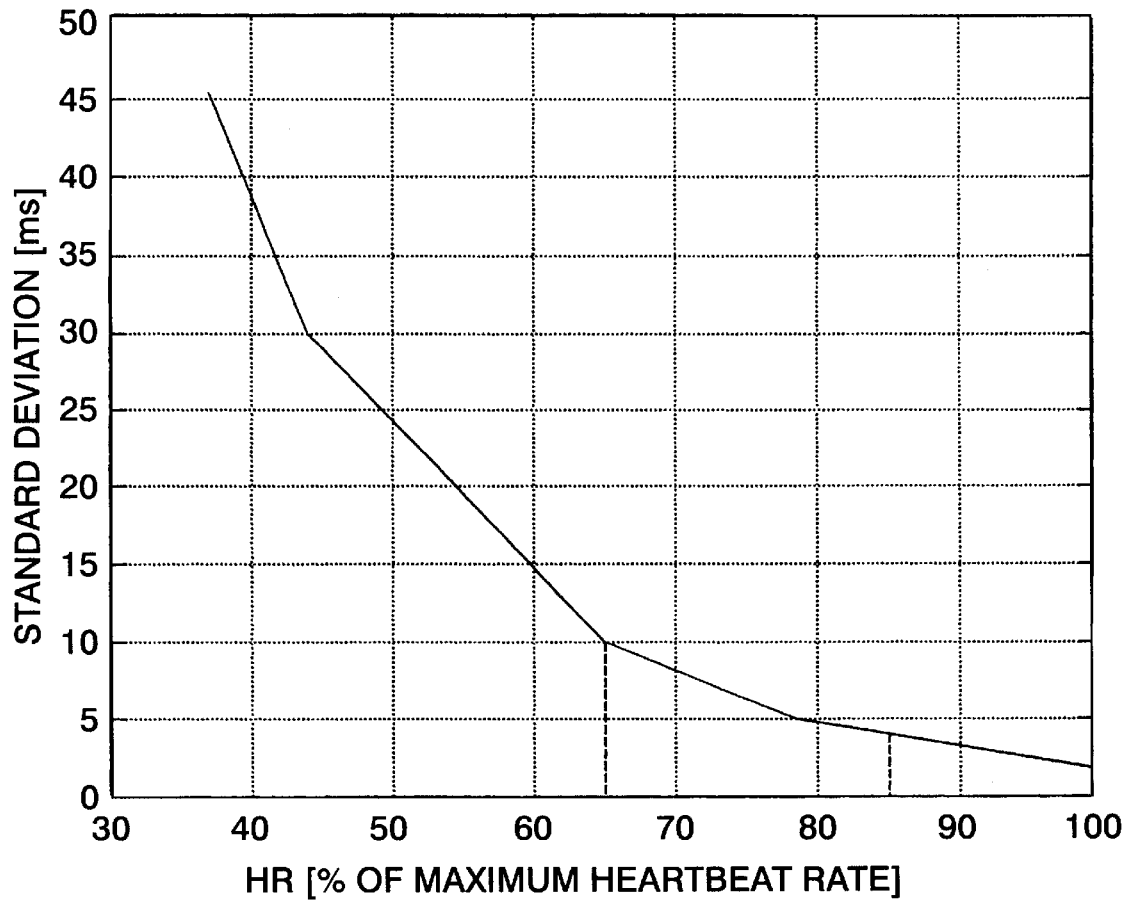
FIG. 2 shows a heartbeat rate variation graph during exertion.

FIG. 2 shows the behaviour of heartbeat rate variation according to the level of exertion. The graph is drawn on the basis of standard deviations calculated from 100 successive R—R intervals. The figure shows a distinct non-linear decrease in the variation when the exertion is increased.

In the method of the invention, an ECG signal is measured at the chest or some other body part of a person engaged in exercise, and this signal is transmitted to a receiver as in existing heartbeat rate monitors. The resolution of the heartbeat rate transmitter in defining the timing information of successive ECG signals is at least in the range of 1 ms. The heartbeat rate of the exercising person is constantly monitored during the entire performance. The heartbeat rate monitor measures, as deviating from averaging monitors, some unambiguous timing point of each ECG signal, for instance the R—R interval obtained from QRS complexes, and calculates the standard deviation of the heartbeat rate or some other variation index from the collected intervals. The heartbeat rate monitor constantly monitors the development of the variation.

Figure 3:
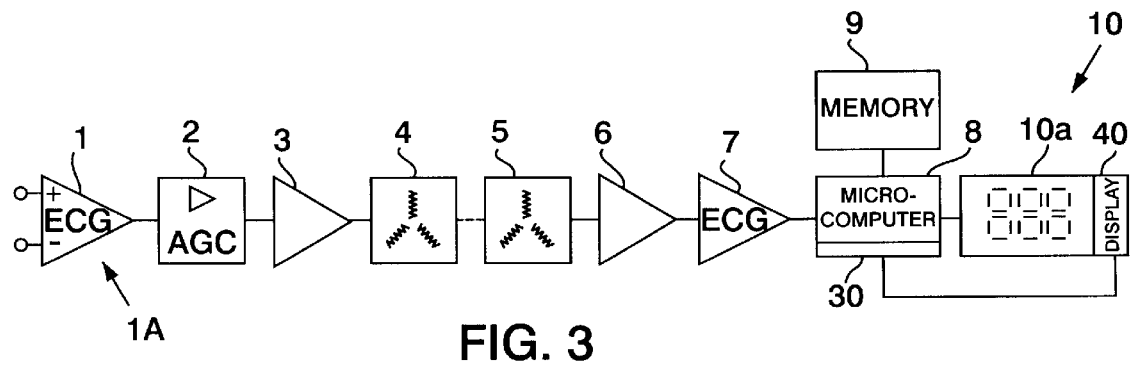
FIG. 3 shows a general view of the apparatus of the invention.

FIG. 3 shows a schematic view of the exemplifying apparatus of the invention. In the telemetric heartbeat rate monitor shown in FIG. 3, ECG electrodes la are connected to the differential input poles of an ECG pre-amplifier 1. The heartbeat rate signal provided by the pre-amplifier 1 is amplified in an AGC amplifier 2, which is used for controlling a power amplifier 3, in which is produced a heartbeat rate signal controlling coils 4, the interval between the pulses of the signal being the same as the interval between the heart pulsations. A magnetic field varying with the rhythm of the heartbeat rate is thus generated in the coils 4. The blocks 1–4 of FIG. 1 preferably constitute a telemetric transmitter unit, such as a transmitter belt, which a person wears against his skin, for instance against his chest.

In FIG. 3, the other blocks, beginning from block 5, constitute a telemetric receiver unit, which is preferably for instance a receiver wristband worn on the wrist. The magnetic field received from the coils 4, detected by receiving coils 5, is amplified in a sensitive pre-amplifier 6, whereafter the signal is applied to a signal amplifier 7. The output signal of the amplifier is processed in a microcomputer 8, which calculates from a desired number of previous pulses an average heartbeat rate, which is indicated, i.e. displayed, on a display 10, such as a liquid crystal display 10 in a display element 10a. The average heartbeat rate can also be stored in a memory 9. As regards the above-mentioned elements 1–10, the apparatus corresponds to known apparatuses.

The most essential part of the invention is a block 30 and a display element 40, to which the block 30 is connected. The block 30 is a means for calculating the heartbeat rate variation. The means 30 can be implemented as a program segment of the microcomputer 8. The means 30 calculates the heartbeat rate variation data and indicates the heartbeat rate variation in the display element 40. In practise, the display element 10a for indicating the average heartbeat rate and the display element 40 for indicating the heartbeat rate variation are different display elements included in the same display unit 10, such as a liquid crystal display.

Figure 4:
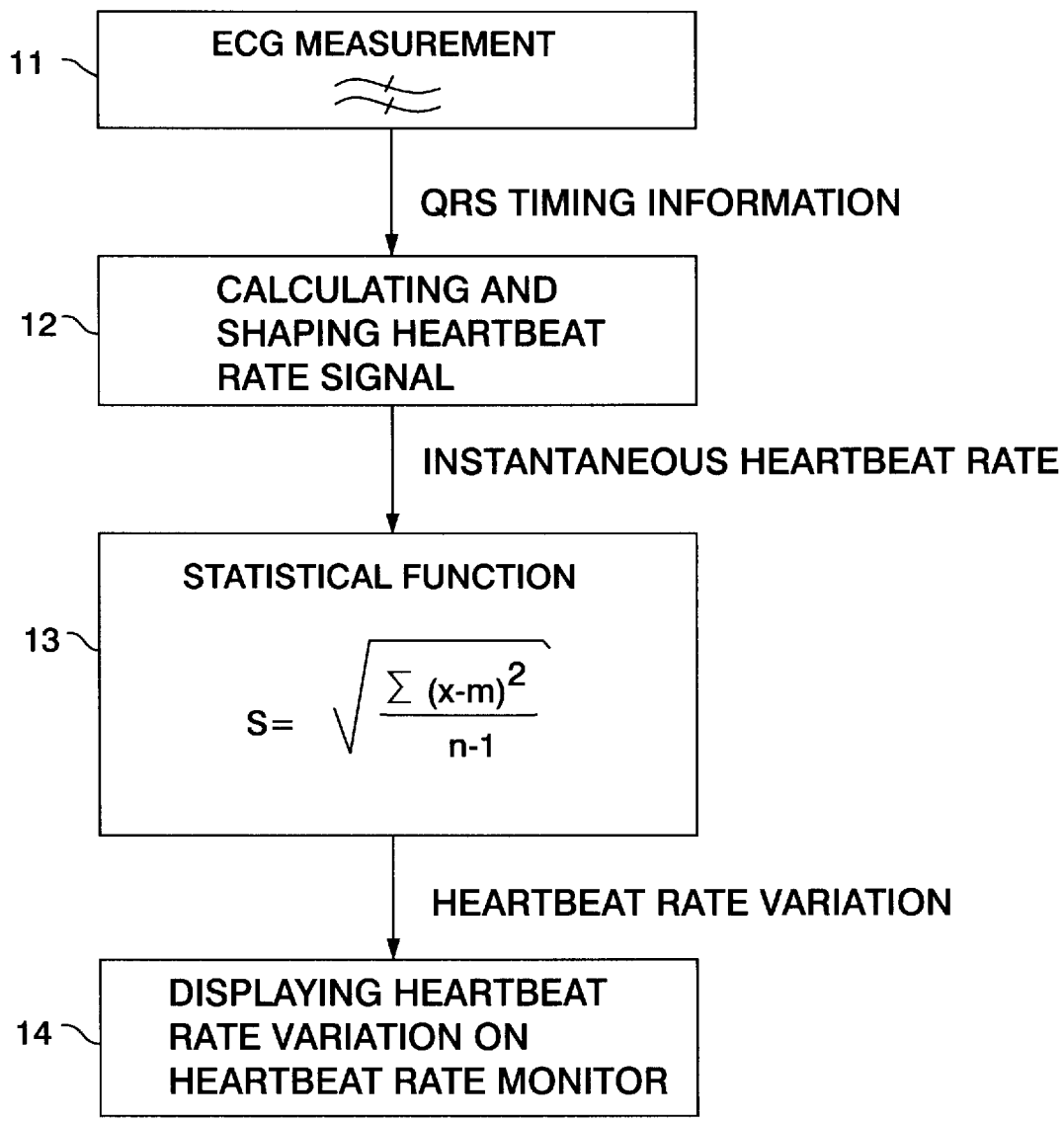
FIG. 4 shows a functional diagram of the apparatus according to an embodiment of the invention.
Figure 5:
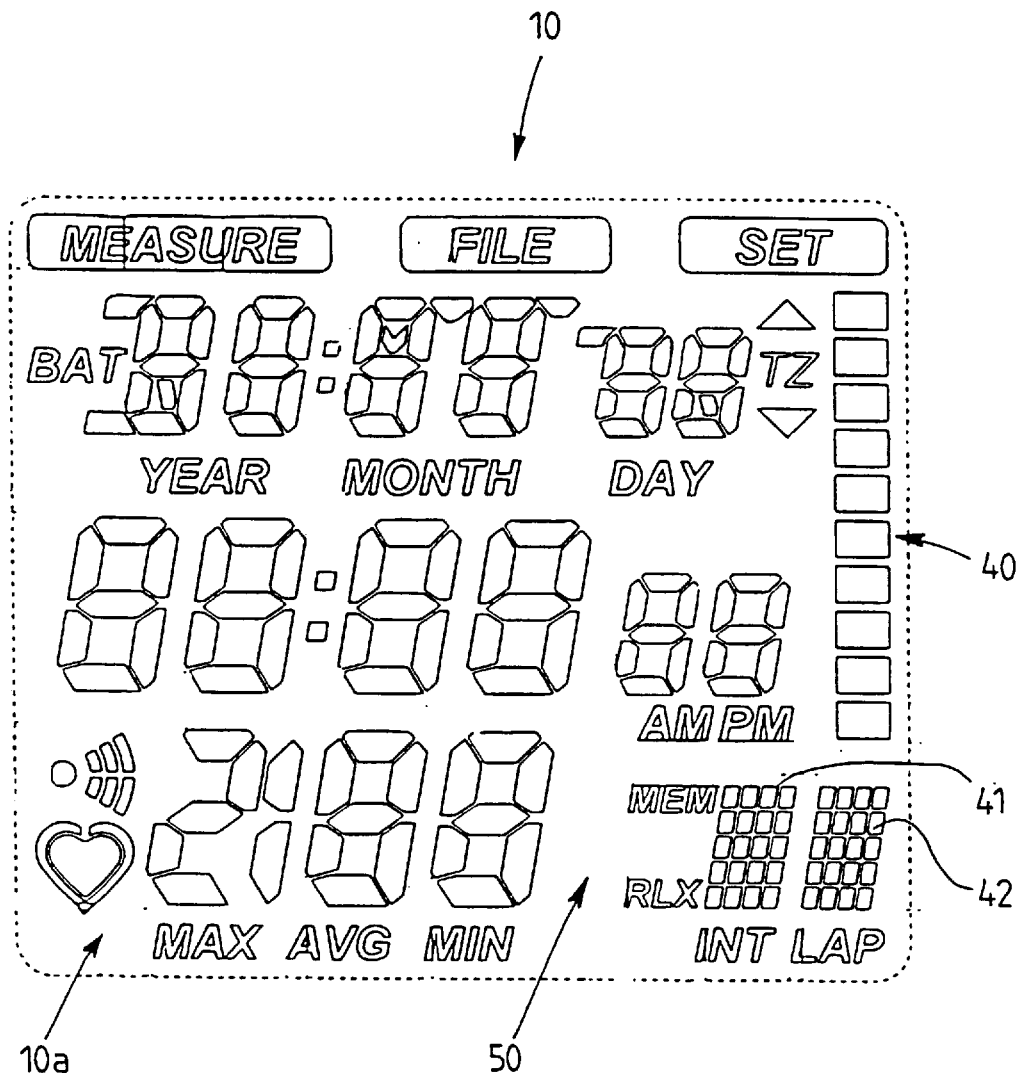
FIG. 5 shows the display of a heartbeat rate monitor.

FIG. 4 shows a functional diagram of the apparatus according to an embodiment of the invention. The functions according to the diagram are preferably included in the software of the microcomputer 8 of the heartbeat rate monitor. The purpose is to determine the heartbeat rate variation of a person engaged for instance in exercise or sports training. In FIG. 4, the heartbeat rate measurement which is the basis of the operation is carried out in block 11. By means of the heartbeat rate monitor 5–10, the heartbeat rate of a person and the timing moment of at least one waveform of the ECG signal, for instance the QRS complex, are measured during the training period.

Thereafter, instantaneous heartbeat rate is calculated in block 12 on the basis of corresponding ECG signal waveform distances, and a possible shaping is carried out for instance with a suitable digital filter. The heartbeat rate signal can be preferably high pass filtered in this connection to remove slow processes distorting the result, these processes being due for instance to sudden changes in load levels.

A heartbeat rate variation value proportional to the magnitude of the heartbeat rate variation or to that of the total or partial power of a spectrum derived from the heartbeat rate is provided by means of a statistical function 13, i.e. by the formula of the standard deviation S in this example. The heartbeat rate variation can also be calculated for instance by means of the height or width of the heartbeat rate variation distribution pattern or by means of a quantity provided by a statistical function derived from the height and width. The block 13 of FIG. 4 corresponds to the block 30 in FIG. 3.

Figure 6A:
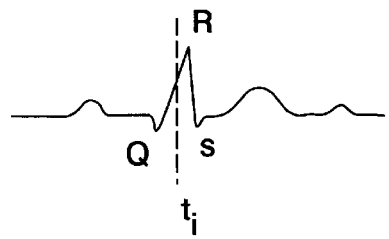
FIGS. 6a–6e show the forming of a heartbeat rate variation signal from an ECG signal.
Figure 6B:
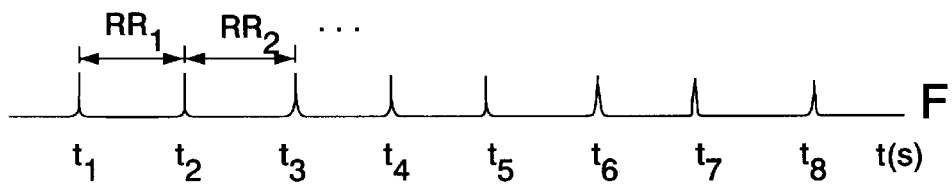
Figure 6C:
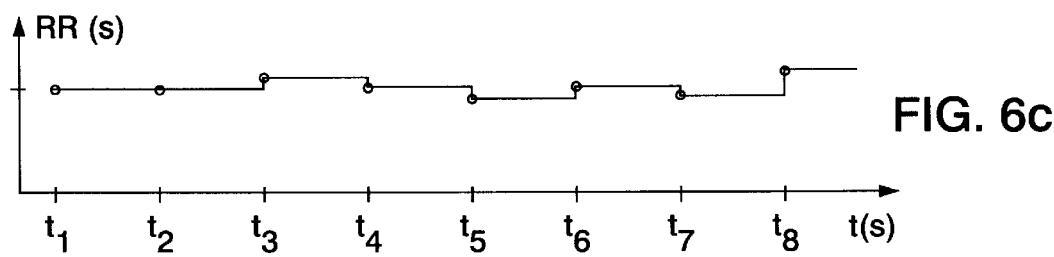
Figure 6D:
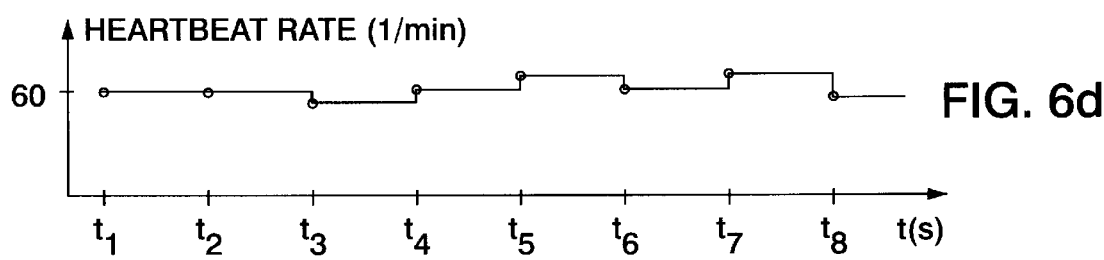
Figure 6E:
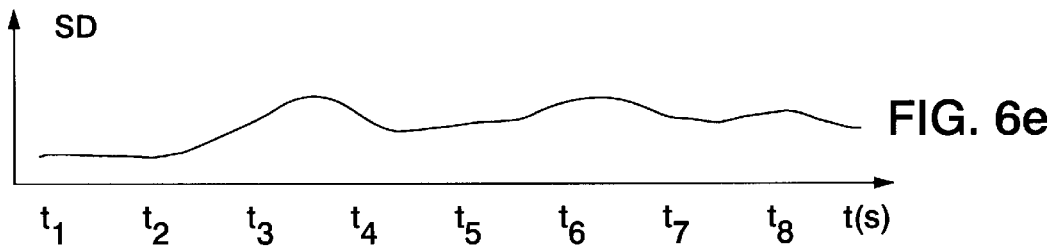

The heartbeat rate variation values calculated during the training period are registered, i.e. stored, in the memory 9 in a block 14 as a time function, and the heartbeat rate variation information is also displayed on the display element 40 of the display 10. The heartbeat rate monitor of the invention thus comprises a heartbeat rate variation calculation unit 30 and a display element 40, which displays, on a real-time basis, an index number and/or a graphic indicator proportional to the heartbeat rate variation, for instance a bar 40, the height of which is in some manner proportional to the calculated heartbeat rate variation. FIGS. 6a–6e show examples of how a heartbeat rate variation signal is derived from an ECG signal. The starting point is the measured ECG signal according to FIG. 1, in which a suitable timing point $t_i$ (FIG. 6a) is determined on the basis of R pulses. FIG. 6b shows the determination of instantaneous heartbeat rate on the basis of the timing points $t_1 \ldots t_n$ of R—R intervals. The instantaneous heartbeat rate is shown as a continuous signal in an R—R time domain in FIG. 6c and in a heartbeat rate time domain in FIG. 6d, the heartbeat rate equalling 60/RR in the heartbeat rate time domain. FIG. 6e shows a heartbeat rate variation graph, which can be calculated directly from the R—R intervals (FIG. 6b) as a recursively floating standard deviation, or as a moving height or width determined from the shape of the distribution pattern, or as a value of the partial or total power of a spectrum derived from the signals of FIG. 6c or 6d.

In the apparatus of the invention, the heartbeat rate variation display 40, i.e. a so-called relaxation display 40, preferably consists of a bar comprising for instance 10 parts. The height of the bar directly represents the standard deviation of pulsation intervals. The higher the bar, the greater the standard deviation and correspondingly the degree of relaxation.

In the preferred embodiment of the invention, the heartbeat rate variation is indicated on the display 10 of the heartbeat rate monitor simultaneously with the average heartbeat rate in the method. The user is thus able to detect both the average heartbeat rate and the heartbeat rate variation at the same time at a single glance, the heartbeat rate variation thus indicating the degree of relaxation of the person.

In the preferred embodiment of the invention, the heartbeat rate variation information is indicated on the display of the heartbeat rate monitor graphically and/or digitally in the method. The graphic display is implemented for instance with a bar-like display element.

The digital display can be implemented with display elements 41–42.

In the method, the heartbeat rate variation information is indicated on the display of the heartbeat rate monitor simultaneously both graphically and digitally.

The heartbeat rate variation information is indicated on such a common display element that is also used for indicating the modes and set conditions of the heartbeat rate monitor.

In the method, an indicator 50 indicates whether the common display element 40 displays heartbeat rate variation information or modes and set conditions.

Even if the invention has been described above with reference to the examples according to the accompanying drawings, it will be apparent that the invention is not so restricted, but it can modified in various ways within the scope of the inventive concept disclosed in the appended claims.

What is claimed is:

1. A method in connection with measuring the heartbeat rate of a person, comprising the following steps:
    measuring the ECG signal of the person and the timing moment of at least one ECG signal waveform,
    calculating the average heartbeat rate from the ECG signal,
    providing, by means of a mathematical function, real-time heartbeat rate variation information proportional to one of the magnitude of the heartbeat rate variation, the total power of a spectrum derived from the heartbeat rate and the partial power of a spectrum derived from the heartbeat rate, and
    displaying in real time said heartbeat rate variation information.

2. A method according to claim 1 further comprising the additional step of displaying the heartbeat rate variation information simultaneously with the average heartbeat rate.

3. A method according to claim further comprising the additional step of indicating the heartbeat rate variation information at least one of graphically and digitally.

4. A method according to claim 3, wherein the heartbeat rate variation information is indicated simultaneously both graphically and digitally.

5. A method according to claim 1, wherein in said step of providing the heartbeat rate variation information, the heartbeat rate variation information is calculated by means of a statistical function which provides the standard deviation of the heartbeat rate as a result.

6. A method according to claim 1, wherein in said step of providing the heartbeat rate variation information, the heartbeat rate variation information is calculated by means of a statistical function which provides one of the height and width of the distribution pattern of one of an instantaneous heartbeat rate signal and R—R signal as a result.

7. A method according to claim 1, wherein in said step of providing the heartbeat rate variation information, the heartbeat rate variation information is calculated from a continuous heartbeat rate signal.

8. A method according to claim 1 including the step of constantly monitoring development of the heartbeat rate variation.

9. A method according to claim 1, including the steps of generating a magnetic field varying with the rhythm of the heartbeat rate with a telemetric transmitter unit and detecting said magnetic field with a telemetric receiver unit, said steps of calculating the average heartbeat rate frequency, providing real time heartbeat rate variation information and displaying said heartbeat rate variation information being performed by said telemetric receiver unit.

10. A method as described in claim 9 including the steps of positioning said telemetric transmitter unit near the chest of the person and securing said telemetric receiver unit to a wrist of the person.

11. An apparatus in connection with measuring the heartbeat rate of a person, the apparatus comprising:
    means for detecting and transmitting heartbeat signals,
    a heartbeat rate monitor for receiving, calculating and measuring said heartbeat signals, and for registering the timing moment of at least one ECG signal waveform contained by a heartbeat signal,
    means for calculating on a real-time basis the average heartbeat rate on the basis of the ECG signal,
    means for providing real-time heartbeat rate variation information proportional to one of the magnitude of the heartbeat rate variation, the total power of a spectrum derived from the heartbeat rate and the partial power of a spectrum derived from the heartbeat rate by means of a mathematical function, and
    means for indicating in real time the heartbeat rate variation information on the heartbeat rate monitor.

12. An apparatus according to claim 11, wherein the means for indicating the heartbeat rate variation information on the heartbeat rate monitor comprises a display element which also indicates the average heartbeat rate information.

13. An apparatus according to claim 11, wherein the means for indicating the heartbeat rate variation information comprises at least one of a graphic and digital display element.

14. An apparatus according to claim 11, wherein the means for indicating the heartbeat rate variation information comprises a display element which also indicates modes and set conditions on the heartbeat rate monitor.

15. An apparatus according to claim 11, further comprising a high pass filter for filtering a heartbeat rate signal.

16. An apparatus according to claim 11, wherein said means for detecting and transmitting heartbeat signals comprises a telemetric transmitter unit and said heartbeat monitor comprises a telemetric receiver unit, said telemetric transmitter unit including means for generating a magnetic field varying with the rhythm of the heartbeat rate, said telemetric receiver unit including means for detecting the magnetic field generated by the telemetric transmitter unit.

17. An apparatus according to claim 16, wherein said heartbeat rate monitor includes means for constantly monitoring development of heartbeat rate variation.

18. A method of providing information relating to the heartbeat of a person, comprising:
    measuring the ECG signal of the person and the timing moment of at least one ECG signal waveform,
    providing, from the ECG signal, a pulse sequence wherein each pulse is representative of a heartbeat of the person, said pulse sequence having intervals between the pulses of said pulse sequence,
    calculating on a real time basis the average heartbeat rate from the pulse sequence derived from the ECG signal,
    providing, by means of a mathematical function, real time heartbeat interval variation information proportional to one of the magnitude of the heartbeat interval variation, the total power of a spectrum derived from the heartbeat rate and the partial power of a spectrum derived from the heartbeat rate, and displaying in real time said heartbeat interval variation information.

19. A method as described in claim 18, wherein each pulse corresponds to an R peak of an ECG signal.

20. A method as described in claim 18 including the step of displaying said heartbeat interval variation and said average heartbeat rate simultaneously.

21. A method as described in claim 18 including the steps of detecting said ECG signal with a telemetric transmitter unit and displaying said heartbeat interval variation information on a telemetric receiver unit worn by the person.

22. An apparatus for measuring the heartbeat rate of a person and providing heartbeat interval variation information, comprising:

means for detecting and transmitting heartbeat signals, a receiver unit for receiving said heartbeat signals and for registering the timing moment of at least one ECG signal waveform contained by a heartbeat signal, and for providing from the ECG signal, a pulse sequence wherein each pulse is representative of a heartbeat of the person, said pulse sequence having intervals between the pulses of said pulse sequence, means for calculating on a real time basis the average heartbeat rate on the basis of the ECG signal, means for providing real time heartbeat interval variation information proportional to one of the magnitude of the heartbeat interval variation, the total power of a spectrum derived from the heartbeat rate and the partial power of a spectrum derived from the heartbeat rate, wherein the heartbeat interval variation is based on collected intervals between the pulses of said pulse sequence, and means for indicating, in real time, said heartbeat interval variation information.

23. An apparatus as described in claim 22, wherein said intervals between heartbeat signals correspond to the R—R intervals obtained from QRS complexes of individual ECG signals.

24. An apparatus as described in claim 22, wherein said means for detecting and transmitting heartbeat signals is a telemetric transmitter unit, said apparatus includes a telemetric receiver unit, said means for calculating, means for providing and means for indicating being incorporated in said telemetric receiver unit.

* * * * *

UNITED STATES PATENT AND TRADEMARK OFFICE
CERTIFICATE OF CORRECTION

PATENT NO.   : 5,840,039
DATED        : November 24, 1998
INVENTOR(S)  : Heikkilä

It is certified that error appears in the above-indentified patent and that said Letters Patent is hereby corrected as shown below:

<u>In Column 5, Line 42,</u>     the patent now reads
"according to claim further"

this should read
--according to claim 1 further--

Signed and Sealed this

Twenty-third Day of March, 1999

Attest:

Q. TODD DICKINSON

Attesting Officer       Acting Commissioner of Patents and Trademarks